United States Patent [19]

Shillington

[11] Patent Number: 4,972,950
[45] Date of Patent: Nov. 27, 1990

[54] SECURE DISPOSABLE CONTAINER ASSEMBLY

[75] Inventor: Richard A. Shillington, Leucadia, Calif.

[73] Assignee: Med-Safe Systems, Inc., Carlsbad, Calif.

[21] Appl. No.: 368,594

[22] Filed: Jun. 20, 1989

[51] Int. Cl.$^5$ .................. A61M 5/32; B65D 83/10
[52] U.S. Cl. .................. 206/366; 206/370; 220/908; 220/404; 220/410; 220/408
[58] Field of Search ............... 206/366, 370; 220/1 T, 220/404, 410, 408

[56] References Cited

U.S. PATENT DOCUMENTS

| | | | |
|---|---|---|---|
| 4,494,652 | 1/1985 | Nelson et al. | 206/366 |
| 4,576,281 | 3/1986 | Kirksey | 206/366 |
| 4,657,139 | 4/1987 | Hanifl | 206/366 |
| 4,662,516 | 5/1987 | Baker, Sr. et al. | 206/366 |
| 4,667,821 | 5/1987 | Shillington | 206/366 |
| 4,702,385 | 10/1987 | Shillington et al. | 220/1 T |
| 4,809,850 | 3/1989 | Laible et al. | 206/366 |

*Primary Examiner*—Joseph Man-Fu Moy
*Attorney, Agent, or Firm*—Baker, Maxham, Jester & Meador

[57] ABSTRACT

A secure disposable container assembly for medical sharps and waste comprises the combination of a substantially rigid box-like housing defined by upstanding front and back complementary half shells hinged togethr along normally vertical side edges defining front, back, and side walls terminating with a top having an upwardly extending circular opening for receiving and providing access to an opening in a disposable container within the housing, a semi-circular peripheral support ledge in the housing closely adjacent the circular opening for supporting a disposable container, a semi-rigid disposable containr having upstanding side walls terminating at a top having a circular opening with a one-way closure therein disposed in the circular opening, and having a circular rim adjacent the top for engagement and support of the container on the peripheral support ledge in the housing.

16 Claims, 2 Drawing Sheets

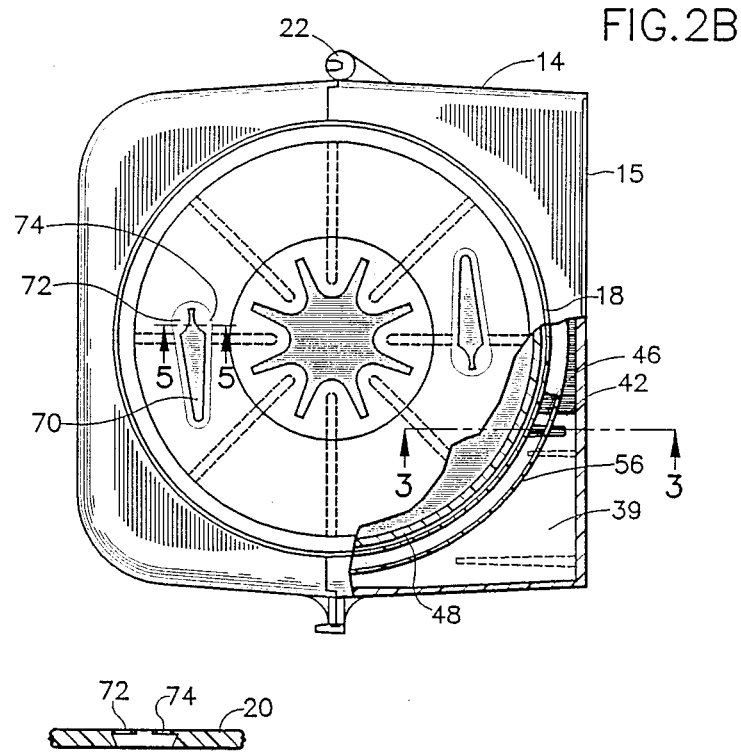
FIG. 5
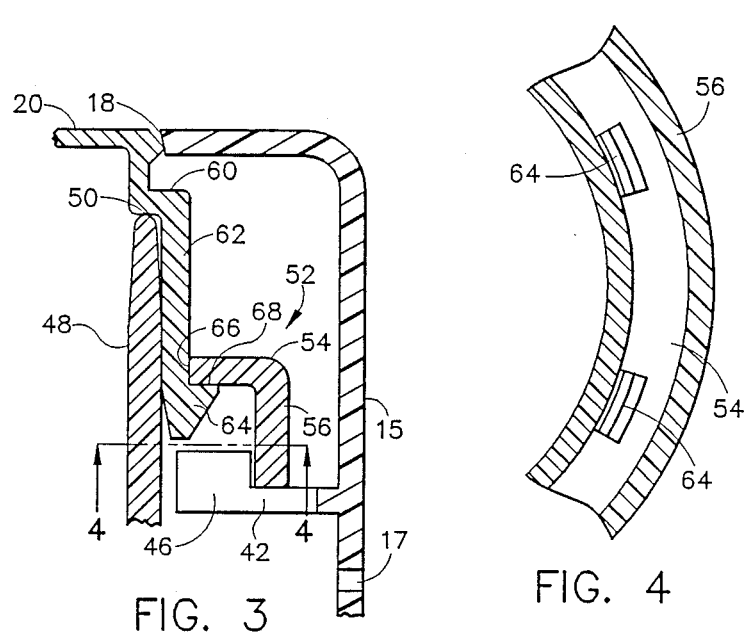

SECURE DISPOSABLE CONTAINER ASSEMBLY

BACKGROUND OF THE INVENTION

The present invention relates to disposable containers for hospital sharps and waste, and pertains particularly to a securable disposable container assembly for disposition of hospital sharps, objects and wastes.

Hospitals and clinics use great quantities of sharps, such as needles, syringes, surgical blades, and the like, that are disposed of rather than cleaned and reused. It is necessary that the sharps be disposed of in a manner that prevents them from falling into the hands of those, such as drug users and the like, that may use them without proper sterilization.

Numerous containers have been developed in recent years, which are disposable for receiving and disposing of hospital sharps, wastes and the like. Many of these containers however do not provide adequate security against pilfering of used syringes and the like from such containers. While containers have been developed which cannot readily be reopened and articles cannot be easily removed therefrom, such containers must be kept in a secure place to prevent unauthorized removal.

In prior U.S. Pat. No. 4,702,385, of which I am co-inventor, we disclose a security mounting device for disposable containers. That device includes a metal mounting bracket, with a complex metal latching arrangement for securely latching a disposable container within a secured container housing. While that prior device is suitable for many applications, certain improvements are desirable.

It is, therefore, desirable that an improved securable disposable container assembly be provided.

SUMMARY AND OBJECTS OF THE INVENTION

It is the primary object of the present invention to provide an improved securable disposable container assembly.

In accordance with a primary aspect of the present invention, a securable disposable container assembly comprises a housing for securely mounting to a support member and having an opening front for receiving a disposable container, with an open top for providing access to an opening in the top of the disposable container. Means are provided for locking the housing to prevent removal of the container.

BRIEF DESCRIPTION OF THE DRAWING

The above and other objects and advantages of the present invention will become apparent from the following description when read in conjunction with the accompanying drawings wherein:

FIGS. 2A and 2B are each a top plan view of the embodiment of FIG. 1 with different portions broken away to reveal different respective details;

FIG. 3 is a detailed partial view is second taken on line 3—3 of FIG. 2;

FIG. 4 is a detailed partial view in section taken on line 4—4 of FIG. 3; and

FIG. 5 is a section view taken along line 5—5 of FIG. 2B.

DETAILED DESCRIPTION OF A PREFERRED EMBODIMENT

Figure 1:
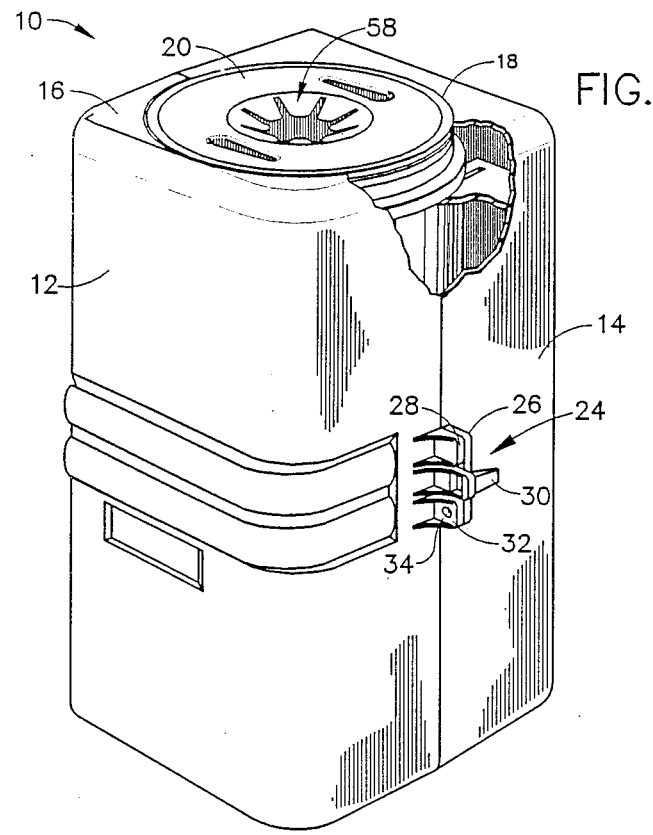
FIG. 1 is a perspective view of an exemplary embodiment of the invention with portions broken away to reveal details.

Referring to FIG. 1 of the drawing, there is illustrated an exemplary embodiment of the invention, which comprises an outer generally rectangular box-like housing, designated generally by the numeral 10. The outer housing in its preferred form is formed of two substantially identical half shells, being a front shell 12 and a back shell 14 defining front and back walls and opposed side walls. The two shells are also formed with a top 16 having a generally planar configuration, with a semi-circular cut out in each shell forming a centrally disposed circular opening 18 for receiving and exposing the top 20 of a disposable container 48, as will be described. The circular opening or edge 18 overlaps a portion of the top of the disposable container 48 within the housing for retaining it in place. The back half shell 14 of the housing (FIG. 3) has a generally planar vertical wall 15, which is formed with suitable mounting bracket means, including for example screw holes or the like 17 for attachment to a suitable vertical support surface (not shown). The front housing is hinged to the back housing along one vertical side edge by suitable hinges 22, and is provided with suitable latching and locking means along the opposite side edge. The housing is preferably molded of a durable substantially rigid plastic, with the hinges and latching and locking assemblies integral therewith.

The latch and lock assembly 24 of the housing comprises a rectangular tab 26 on the back shell 14, which is abutted by an upper tab 28 on the front shell 12. A latch hook 30, with an elongated releasing finger, releasably hooks over the tab 24. A locking tab 32 on the front shell 12 includes a lock bore 34, aligned with a bore 36 on tab 26 for receiving a padlock for locking the housing in the closed position.

The back wall assembly or back housing assembly includes a support ledge and latch assembly in the form of a pair of ledges 38 and 39 extending inside, just below the top of the housing for engagement by a support rim of a disposable container. The support ledges 38 and 39 are semi-circular and formed on the interior of the back shell 14. It includes latching fingers 40 and 42 at a back position thereof, having upwardly extending knobs or hooks 44 and 46 for latchably engaging the rim of the disposable container, as will be described.

The housing is designed to receive generally cylindrical disposable containers of the type such as illustrated and described in the previously mentioned patent.

Referring to FIGS. 1, 2 and 3, a generally cylindrical disposable container 48 is illustrated within the outer housing, having a number of improved features for use in the present assembly. In FIG. 1, a portion of the outer housing is broken away to show the top of the disposable container 48, and its support within the outer housing. As illustrated, the container is of a generally cylindrical, but slightly tapered configuration, defined by a generally vertical upstanding generally circular wall. The wall has a slightly larger diameter at the upper end, which is open to present an upwardly open top, with a peripheral rim 50 on which is mounted a closure assembly.

Disposed just below the upper rim or edge 50 is an outwardly extending reinforcing and support rim 52, which is provided to enable the construction of the walls of the container of a very minimum amount of material and yet provide a semi-rigid container for suitable use herein. The reinforcing rim comprises an annular outwardly or radially extending portion 54, with a downwardly depending lip or skirt 56. This downwardly depending lip provides means for engaging the support ledge 38 and 39 of the back housing member, and for latchably engaging the latch fingers 40 and 42, and latch bumps 44 and 46 therein.

An improved closure or top assembly for the disposable container is also provided, and comprises a generally circular closure member 20, preferably having a central one-way closure designated generally as 58, as in the prior patent. The top or closure member has an outer downwardly depending stepped rim, which includes a first step 60, that overlaps the upper peripheral edge 50 of the side wall of the container, and a second skirt portion 62 extending downward to the container rim 54.

Figure 2A:
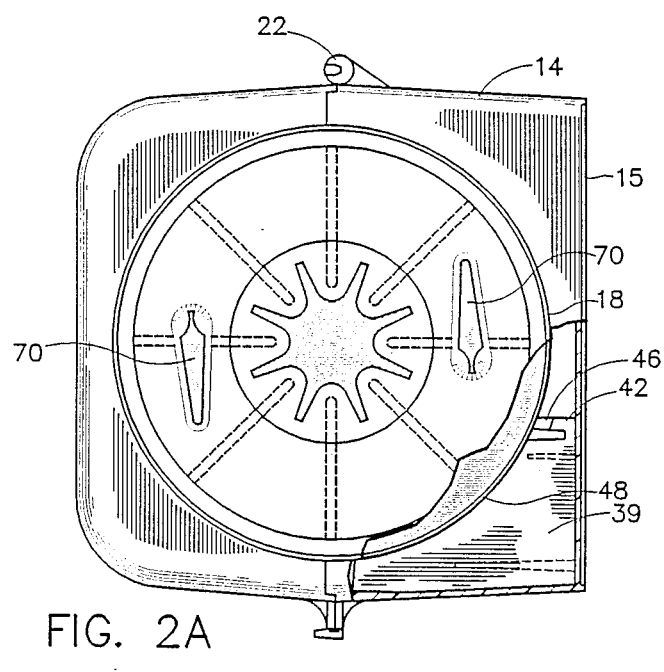

In FIG. 2A, the outer housing and inner container is broken away down to the upper surface of support ledge 39. This illustrates the curvature of ledge 39 along a curve closely conforming to the curvature of the wall of the container 48. It also more clearly illustrates latch finger 42 and the latch bump 46, which engages under lip 56 (FIG. 3).

Referring to FIG. 2B, in the lower right quadrant, the outer housing and inner container is broken away down to the top of the skirt 56 of reinforcing and support rim 54. This illustrates the support skirt 56 of rim 54 overlapping a portion of the support ledge 39 and the latch knob or bump 46.

Referring to FIGS. 3 and 4, the skirt 62 includes a plurality of latching tabs 64 extendable into and through a plurality of slots 66 in the disposable container rim 54, for permanently attaching the top member 20 to the disposable container. The latch members 64 have a wedge shaped tip, with a hook member hooking underneath the radially extending flange or rim 54 of the disposable container. The top or upper rim edge 50 of the container sealingly engages the step portion 60 of the closure or top, providing a watertight seal.

The top is also preferably provided with improved needle removal slots 70, as illustrated, having a generally tear-drop configuration tapered for wedged engagement with the hub of a syringe needle for enabling the threaded removal thereof. The large end of the slot is provided with a pair of opposed thin fingernail like engaging edge 72 and 74 for engaging the unthreaded hub of the needle for applying a force thereto for removal thereof. Such fingernail like edges are shown for example in another type removal slot in my prior U.S. Pat. No. 4,667,821, entitled "Swivel Top Closure for Phlebotomy Container", which is incorporated herein by reference as though fully set forth. A permanent closure 76, as in my previous patent, provides for permanent closure of the disposable container when filled.

In operation, a housing, as described above, is selected and mounted in a suitable position on a suitable support structure, such as a vertical wall or other suitable surface. A disposable container of the above described type, having a suitable support rim and the like, is selected and inserted in the back shell of the housing. The open top with one-way closure of the disposable container is positioned in the circular opening 18 of the housing. This provides access for insertion of disposable articles into the disposable container. The hinged front shell is then pivoted to its closed position and locked to secure the disposable container within the housing.

After suitable use, such that the disposable container is substantially filled, the outer housing may be opened by removing the padlock and unlatching the latch assembly 24 and swinging the front portion 12 outward. The disposable container rim is unlatched by engaging the lower end of the housing and pushing inward, tilting the upper portion of the container backward, lifting the rim edges 56 off and above the latching fingers 40 and 42, such that the container may then be pulled directly outward. The permanent closure of the container is then secured in place over the top 20 and on a one-way closure 58. An empty container may be then inserted in the housing and re-closed and locked, as previously explained.

While I have illustrated and described my invention by means of specific embodiments, it is to be understood that numerous changes and modifications may be made therein without departing from the spirit and scope of the invention as defined in the appended claims.

I claim:

1. A secure disposable container assembly comprising:
    a generally box-like housing having a front with means defining a front opening for receiving a disposable container and a closure for said opening, a back having mounting means for mounting on a vertical support means, and a top having a top opening for providing access to an opening in a disposable container in said housing, said housing is bisected along a longitudinal vertical axis into front and back half shells for defining said front opening and said closure, and said top opening comprises adjacent semi-circular openings in a top of said half shells;
    mounting means in said housing adjacent said top for detachably mounting a disposable container therein by flange means near a top of said container; and
    locking means for locking said closure for securing a disposable container in said housing.

2. A secure disposable container assembly according to claim 1 wherein:
    said mounting means comprises an inwardly extending ledge for engaging a peripheral flange on a disposable container, and latching means for detachably engaging and latching to said peripheral flange.

3. A secure disposable container assembly according to claim 1 further comprising:
    a semi-rigid container detachably mounted in said housing, said container is defined by upstanding substantially cylindrical walls terminating in a circular rim defining an upwardly extending top opening, a one-way pass through closure covering said opening, and outwardly extending reinforcing and support flange encircling said cylindrical wall below said rim for supporting said container within said housing.

4. A secure disposable container assembly comprising:
    a generally box-like housing having a front with means defining a front opening for receiving a disposable container and a front closure for said opening, a back having mounting means for mounting on a vertical support means, and a top having a top opening for providing access to an opening in a disposable container in said housing;

mounting means in said housing adjacent said top for detachably mounting a disposable container therein by flange means near a top of said container;

a semi-rigid container detachably mounted in said housing, said container is defined by upstanding substantially cylindrical walls terminating in a circular rim defining an upwardly extending top opening, a one-way pass through closure covering said opening, an outwardly extending reinforcing and support flange encircling said cylindrical wall below said rim, said pass through closure includes an annular skirt extending downward over said circular rim and terminating in a lower edge having a plurality of locking tabs extending into corresponding slots in said reinforcing and support flange for retaining said pass through closure in place on said container; and locking means for locking said front closure for securing a disposable container in said housing.

5. A secure disposable container assembly comprising:

a housing having a generally rectangular box-like configuration defined by a pair of complementary half shells defining a front shell and a back shell, said back shell having mounting means for mounting on a support structure, said front shell being hinged to said back shell and defining said front opening and said closure, and a top having a top opening for providing access to an opening in a disposable container in said housing;

detachable mounting means in said housing comprising an inwardly extending ledge for engaging a peripheral flange on a disposable container, and latching means for detachably engaging and latching to said peripheral flange;

a semi-rigid container detachably mounted in said housing, said container is defined by upstanding substantially cylindrical walls terminating in a circular rim defining an upwardly extending opening, a one-way pass through closure covering said opening, an outwardly extending reinforcing and support flange encircling said cylindrical wall below said rim; and locking means for locking said closure for securing a disposable container in said housing.

6. A secure disposable container assembly according to claim 5 wherein:

said peripheral flange has a downwardly depending skirt defining a circular edge, and said latching means engages said circular edge.

7. A secure disposable container assembly according to claim 6 wherein:

said inwardly extending ledge extends inwardly from said back shell.

8. A secure disposable container assembly for medical sharps and waste comprising:

a substantially rigid housing having front, back and side walls with a top having a circular opening for receiving and providing access to an opening in a disposable container within said housing, said front wall being pivotally hinged to provide an access opening to said housing;

a semi-rigid disposable container removably disposed in said housing and having a top with an opening including a one-way closure disposed in said circular opening;

a support ledge in said housing adjacent said top;

latching tabs on and extending upwardly from said support ledge; and a peripheral support rim on said disposable container adjacent the top thereof for engaging said support ledge and said latching tabs for supporting and latching said disposable container in said housing.

9. A secure disposable container assembly comprising:

a substantially rigid housing having front, back and side walls with a top having a circular opening for receiving and providing access to an opening in a diposable container within said housing, said front wall being pivotally hinged to provide an access opening to said housing;

a semi-rigid disposable container removably disposed in said housing and having a top with an opening including a one-way closure disposed in said circular opening, said one-way closure includes an annular skirt extending downward over said circular rim and terminating in a lower edge having a plurality of locking tabs extending into corresponding slots in said peripheral support rim for retaining said closure in place on said container;

a support ledge in said housing adjacent said top; and a peripheral support rim on said disposable container adjacent the top thereof for engaging said support ledge for supporting said disposable container in said housing.

10. A secure disposable container assembly according to claim 8 wherein:

said semi-rigid container is defined by upstanding substantially cylindrical walls terminating in a circular rim defining an upwardly extending top opening, a one-way pass through closure covering said opening, said peripheral support rim includes downwardly skirt means; and latching means on said support ledge for engaging said skirt for latching said container in position on said ledge.

11. A secure disposable container assembly comprising:

a substantially rigid housing having front, back and side walls with a top having a circular opening for receiving and providing access to an opening in a disposable container within said housing, said front wall being pivotally hinged to provide an access opening to said housing;

a semi-rigid disposable container removably disposed in said housing and defined by upstanding substantially cylindrical walls terminating in a circular rim defining an upwardly extending top opening, a one-way pass through closure covering said opening and disposed in said circular opening;

a support ledge in said housing adjacent said top; and a peripheral support rim on said disposable container adjacent the top thereof including downwardly extending skirt means for engaging said support ledge for supporting said disposable container in said housing, said closure includes an annular skirt extending downward over said circular rim and terminating in a lower edge having a plurality of locking tabs extending into corresponding slots in said peripheral support rim for retaining said closure in place on said container.

12. A secure disposable container assembly according to claim 11 wherein:

said housing is bisected along a longitudinal vertical axis into front and back half shells for defining said front opening and said closure, and said top opening comprises adjacent semi-circular openings in a top end of said half shells.

13. A secure disposable container assembly for medical sharps and waste comprising in combination:
   a substantially rigid box-like housing defined by upstanding front and back complementary half shells hinged together along normally vertical side edges defining front, back, and side walls terminating with a top having an upwardly extending circular opening for receiving and providing access to an opening in a disposable container within said housing;
   a semi-circular peripheral support ledge in said housing closely adjacent said circular opening;
   a semi-rigid disposable container having upstanding side walls terminating at a top having a circular opening with a one-way closure disposed over said circular opening; and
   a circular rim adjacent said top for engagement and support of said container on said peripheral support ledge in said housing.

14. A secure disposable container assembly according to claim 13 wherein:
   said closure includes an annular skirt extending downward over said circular opening and terminating in a lower edge having a plurality of locking tabs extending into corresponding slots in said circular rim for retaining said closure in place on said container.

15. A secure disposable container assembly according to claim 14 wherein:
   said support ledge includes latching means for engaging said skirt for latching said container in position on said ledge.

16. A secure disposable container assembly according to claim 14 wherein said one-way closure comprises:
   frame means for mounting on said upwardly extending circular opening of said semi-rigid disposable container;
   an opening in said frame means having one-way closure means therein for receiving a disposable article; and
   needle removal slot means in said frame means adjacent said opening and comprising an elongated uniformly tapering slot having vertical side walls extending between semi-circular ends of different diameters defining a variable width wrench for engaging and applying torque to the hub of a needle for removal thereof, and wherein the end thereof with the larger of said diameters including pulling means defined by opposing thin edges for engaging between a syringe barrel a needle hub for pulling said unthreaded needle from the bore of a holder.

* * * * *